United States Patent
Paul, III et al.

(10) Patent No.: US 7,205,112 B2
(45) Date of Patent: Apr. 17, 2007

(54) MATERIALS AND METHODS FOR DETECTION OF ENTEROVIRUS AND NOROVIRUS

(75) Inventors: John H. Paul, III, St. Petersburg, FL (US); Erica T. Casper, St. Petersburg, FL (US); Stacey S. Patterson, Tampa, FL (US)

(73) Assignee: University of South Florida, Tampa, FL (US)

( * ) Notice: Subject to any disclaimer, the term of this patent is extended or adjusted under 35 U.S.C. 154(b) by 321 days.

(21) Appl. No.: 10/938,005

(22) Filed: Sep. 10, 2004

(65) Prior Publication Data

US 2005/0048475 A1    Mar. 3, 2005

Related U.S. Application Data

(63) Continuation-in-part of application No. 10/857,109, filed on May 28, 2004, now abandoned, which is a continuation-in-part of application No. 10/179,082, filed on Jun. 25, 2002, now abandoned.

(60) Provisional application No. 60/301,218, filed on Jun. 27, 2001.

(51) Int. Cl.
*C12Q 1/68* (2006.01)

(52) U.S. Cl. .................... 435/6; 435/91.1; 435/91.2

(58) Field of Classification Search .................... None
See application file for complete search history.

(56) References Cited

U.S. PATENT DOCUMENTS

| 6,379,867 B1 | 4/2002 | Mei et al. |
| 2002/0024714 A1 | 2/2002 | Sandstrom et al. |

OTHER PUBLICATIONS

Fox, J.D. "Development and evaluation of nucleic acid sequence based amplification (NASBA) for diagnosis of enterovirus infections using the NucliSens Basic Kit" *J. Clin. Virology*, 2002, 24:117-130.

Casper, E.T. et al. "Development and evaluation of a method to detect and quantify enteroviruses using NASBA and internal control RNA (IC-NASBA)" *J. Virological Methods*, 2005, 124:149-155.
Patterson, S.S. et al. "Increased precision of microbial RNA quantification using NASBA with an internal control" *J. Microbiol. Methods*, 2005, 60:343-352.
Caro, V. et al. "Molecular strategy for 'serotyping' of human enteroviruses" *J. Gen. Virol.*, 2001, 82:79-91.
Casas, I. et al. "Molecular characterization of human enteroviruses in clinical samples: Comparison between VP2, VP1, and RNA polymerase regions using RT nested PCR assays and direct sequencing of products" *J. Med. Virol.*, 2001, 65:138-148.
Heim, A. and Schumann, J. "Development and evaluation of a nucleic acid sequence based amplification (NASBA) protocol for the detection of enterovirus RNA in cerebrospinal fluid samples" *J. Virol. Methods*, 2002, 103:101-107.
Landry, M. et al. "Comparison of the NucliSens Basic Kit (nucleic acid sequence-based amplification) and the argene biosoft enterovirus consensus reverse transcription-PCR assays for rapid detection of enterovirus RNA in clinical specimens" *J. Clin. Microbiol.*, 2003, 41:5006-5010.
Richter, J. et al. "Molecular typing of enteroviruses associated with viral meningitis in Cyprus, 2000-2002" *J. Med. Microbiol.*, 2006, 55:1035-1041.
Thoelen, I. et al. "Analysis of the serotype and genotype correlation of VP1 and the 5' noncoding regions in an epidemiological survey of the human enterovirus B species" *J. Clin. Microbiol.*, 2004, 42:963-971.
Thoelen, I. et al. "Molecular typing and epidemiology of enteroviruses identified from an outbreak of aseptic meningitis in Belgium during the summer of 2000" *J. Med. Virol.*, 2003, 70:420-429.

*Primary Examiner*—Gary Benzion
*Assistant Examiner*—Heather G. Calamita
(74) *Attorney, Agent, or Firm*—Saliwanchik, Lloyd & Saliwanchik (57) ABSTRACT

The invention provides polynucleotides and methods for detecting and quantifying RNA viruses, such as enteroviruses and noroviruses. In one aspect, the invention provides amplification primers and labeled molecular beacons for amplification of viral nucleic acid sequences. In another aspect, the invention provides a synthetic RNA internal control. In another aspect, the invention provides a kit for detecting the presence of enterovirus and/or norovirus in a sample.

14 Claims, 5 Drawing Sheets

SEQUENCE LISTING

<160> NUMBER OF SEQ ID NOS: 10

<210> SEQ ID NO 1
<211> LENGTH: 49
<212> TYPE: DNA
<213> ORGANISM: Artificial Sequence
<220> FEATURE:
<223> OTHER INFORMATION: Primer Ent P1 (JP127)

<400> SEQUENCE: 1
aattctaata cgactcacta tagggagaag gaccggatgg ccaatccaa                49

<210> SEQ ID NO 2
<211> LENGTH: 24
<212> TYPE: DNA
<213> ORGANISM: Artificial Sequence
<220> FEATURE:
<223> OTHER INFORMATION: Primer Ent P2 (JP128)

<400> SEQUENCE: 2
cctccggccc ctgaatgcgg ctaa                                           24

<210> SEQ ID NO 3
<211> LENGTH: 21
<212> TYPE: DNA
<213> ORGANISM: Artificial Sequence
<220> FEATURE:
<223> OTHER INFORMATION: probe for poliovirus

<400> SEQUENCE: 3
tactttgggt gtccgtgttt c                                              21

<210> SEQ ID NO 4
<211> LENGTH: 20
<212> TYPE: DNA
<213> ORGANISM: Artificial Sequence
<220> FEATURE:
<223> OTHER INFORMATION: Primer Ent P3

<400> SEQUENCE: 4
ggtgtccgtg tttccttta                                                 20

<210> SEQ ID NO 5
<211> LENGTH: 32
<212> TYPE: DNA
<213> ORGANISM: Artificial Sequence
<220> FEATURE:

-continued

```
<223> OTHER INFORMATION: EnteroBeacon

<400> SEQUENCE: 5
catgcgtggc tgcttatggt gacaatcgca tg                                  32

<210> SEQ ID NO 6
<211> LENGTH: 20
<212> TYPE: DNA
<213> ORGANISM: Artificial Sequence
<220> FEATURE:
<223> OTHER INFORMATION: Primer Nor 3

<400> SEQUENCE: 6
caatggaatt ccatcgccca                                                20

<210> SEQ ID NO 7
<211> LENGTH: 50
<212> TYPE: DNA
<213> ORGANISM: Artificial Sequence
<220> FEATURE:
<223> OTHER INFORMATION: Primer Nor 4

<400> SEQUENCE: 7
aattctaata cgactcacta tagggagaag ttgtcacgat ctcatcatca               50

<210> SEQ ID NO 8
<211> LENGTH: 30
<212> TYPE: DNA
<213> ORGANISM: Artificial Sequence
<220> FEATURE:
<223> OTHER INFORMATION: NorBeacon

<400> SEQUENCE: 8
catcggacat catacaggct aattccgatg                                     30

<210> SEQ ID NO 9
<211> LENGTH: 92
<212> TYPE: DNA
<213> ORGANISM: Artificial Sequence
<220> FEATURE:
<223> OTHER INFORMATION: Enteroviral Internal Control

<400> SEQUENCE: 9
ggtgtccgtg tttccttta tttttattgc ttagtctcgg gttattttt cacagattgt     60 tatcataaag cgaattggat tggccatccg gt                                  92

<210> SEQ ID NO 10
<211> LENGTH: 33
<212> TYPE: DNA
<213> ORGANISM: Artificial Sequence
<220> FEATURE:
<223> OTHER INFORMATION: Beacon for the Enteroviral Internal Control

<400> SEQUENCE: 10
cgatcgctta gtctcgggtt attttttcga tcg                                 33
```

MATERIALS AND METHODS FOR DETECTION OF ENTEROVIRUS AND NOROVIRUS

CROSS-REFERENCE TO A RELATED APPLICATIONS

This application is a continuation-in-part of U.S. application Ser. No. 10/857,109, filed May 28, 2004 now abandoned, which is a continuation-in-part of U.S. application Ser. No. 10/179,082, filed Jun. 25, 2002 now abandoned, which claims the benefit of U.S. Provisional Application No. 60/301,218, filed Jun. 27, 2001, each of which are incorporated herein by reference in their entireties, including all figures, tables, and sequences.

GOVERNMENT SUPPORT

The subject matter of this application has been supported by a research grant from the Office of Naval Research under grant number N00014-03-1-0753. Accordingly, the government may have certain rights in this invention.

BACKGROUND OF THE INVENTION

Good microbiological water quality in coastal waters is a national priority. With wastewater contaminating such aquatic areas, there is an increased risk of infection. The organisms responsible for infectious risk can include viruses, bacteria, and protozoans. Individuals at risk are those who have increased contact with contaminated water. These individuals nonexclusively include swimmers, divers, and boaters as well as those consuming products harvested from the contaminated water.

Pathogenic organisms such as enteric viruses pose a serious problem to life. Of the enteric viruses, one of the largest and best known groups is that of the enteroviruses, some of them important pathogens for humans and animals. Enteroviruses (EV) are small, non-enveloped, and isometric, belonging to the Picornaviridae family, and their genome consists of a simple chain RNA positive pole molecule (ssRNA+) with approximately 7,400 nucleotides (nt). These are the among the most common animal viruses and infect a large variety of mammals. The viruses are generally transmitted from person to person by ingestion (for example, fecal-oral route) or from exposure to contaminated water supplies. Furthermore, evidence indicates that the viruses can be spread via the respiratory tract. Once exposed, the virus infects the body via the blood stream and multiplies in the gut mucosa.

Approximately 90 serotypes of enteroviruses have been identified, 62 of which infect humans and 27 animals. Bovine enteroviruses (BEV) are broadly distributed all over the world and classified as enzootic in some countries. Two species have been described to date: BEV1 and BEV2 (Knowles, N. J., and Barnett, I. T. (1985), *Arch Virol* 83 (3–4), 141–55), although there are probably more that have not yet been identified. There are 3 species of porcine enteroviruses that have been described. An ovine enterovirus (OEV-1) that is closely linked to the BEVs has been isolated. The existence of viruses has been described in ocean environments, although it is believed that most of the viruses found in natural water are bacteriophages, cyanophages, and other types capable of infecting microalgae. The existence of water contaminated by human enteric viruses has also been described, especially close to urban areas, related to sources of human infections (Chapron et al., 2000, *Appl Environ. Microbiol.* 66:2520–2525; Abbaszadegan et al., 1993, *Appl. Environ. Microbiol.* 59:1318–1324; Abbaszadegan et al., 1999, *Appl. Environ. Microbiol.* 65:444–449; Bosch A., 1998, *Int. Microbiol.* 1:191–196; Pianetti et al., 2000, *Epidemiol. Infect.* 125:455–462; Schvoerer et al., *Res. Microbiol.* 152:179–186).

Most infections occur during childhood. Although the infections are largely transient, they produce lifelong immunity to the organism. A majority of enteroviral infections result in mild illness; however, enteroviruses can cause an array of different diseases affecting many different organs (for example, neurologic (polio, aseptic meningitis, encephalitis), respiratory (common cold, tonsillitis, pharyngitis, rhinitis), cardiovascular (myocarditis, pericarditis), etc.). The ability to detect the presence of the organisms that cause these conditions is beneficial to the health and welfare of those with increased potential of exposure.

There is no specific treatment for enterovirus infections. In infants, enteroviral meningitis is often confused with bacterial or herpesvirus infections resulting in misdiagnosis. Often, children are hospitalized and incorrectly treated with antibiotics and anti-herpes drugs.

While most enteroviral infections are known and documented, these viruses have also been implicated in several chronic diseases, such as juvenile onset of diabetes mellitus, chronic fatigue syndrome, and amyotrophic lateral sclerosis (Lou Gehrig's Disease); however, definitive proof is deficient.

Furthermore, there is a high degree of serological cross reactivity amongst the more than 70 known enteroviruses, which include: Polio 1, 2, 3; Coxsackie A 1–24; Coxsackie B 1–6; ECHO 1–34; Entero 68–71; and Entero 72 (Hepatitis A). To reduce the risk of enteroviral infection, the U.S. EPA proposed legislation mandating the testing of groundwater for the presence of enteroviruses.

Noroviruses (genus *Norovirus*, family Caliciviridae) are a group of related, single-stranded RNA, non-enveloped viruses that cause acute gastroenteritis in humans. *Norovirus* was recently approved as the official genus name for the group of viruses provisionally described as "Norwalk-like viruses" (NLV). This group of viruses has also been referred to as caliciviruses (because of their virus family name) and as small round structured viruses, or SRSVs (because of their morphological features). Another genus of the calicivirus family that can cause gastroenteritis in humans is *Sapovirus*, formerly described as "Sapporo-like virus" (SLV) and sometimes referred to as classical or typical calicivirus.

Noroviruses are named after the original strain "Norwalk virus," which caused an outbreak of gastroenteritis in a school in Norwalk, Ohio, in 1968. Currently, there are at least four norovirus genogroups (GI, GII, GIII, and GIV), which in turn are divided into at least 20 genetic clusters.

Noroviruses are transmitted primarily through the fecal-oral route, either by consumption of fecally contaminated food or water or by direct person-to-person contact. Environmental and fomite contamination may also act as a source of infection. Evidence exists for transmission due to aerosolization of vomitus that presumably results in droplets contaminating surfaces or entering the oral mucosa and being swallowed. Noroviruses are highly contagious, and it is thought that an inoculum bearing very few viral particles is sufficient to infect an individual. During outbreaks of norovirus gastroenteritis, several modes of transmission have been documented; for example, initial foodborne transmission in a restaurant, followed by secondary person-to-person transmission to household contacts. Although presymptomatic viral shedding may occur, shedding usually begins with onset of symptoms and may continue for 2 weeks after recovery.

The isolation and detection of such enteric pathogens is known to be accomplished by reverse transcriptase polymerase chain reaction (RT-PCR) and cell culture (See M. Gilgen et al., (1995) *Appl. Environ. Microbiol.* 61: 1226–31). Both of these techniques have advantages and disadvantages. While RT-PCR is generally faster, more sensitive, and more specific, it cannot distinguish viable from nonviable viruses. Further, currently available primer sets are not specific among the full suite of human enteroviruses. Currently only about 25 of the more than 70 known enteroviruses can be detected by the RT-PCR method. Thus, use of the RT-PCR assay allows sensitive detection but cannot determine whether the resulting amplicon is from one virus, multiple virus strains, a pathogen, or a vaccine.

BRIEF SUMMARY OF THE INVENTION

The instant invention provides an amplification and detection technology for enteroviruses and noroviruses in samples, such as biological and environmental samples, based upon an enzymatic amplification reaction, such as nucleic acid sequence based amplification (NASBA) or RT-PCR. NASBA is an isothermal method of amplifying RNA (Compton, J. *Nature*, 1991, 350(6313):91–92). The process results in an approximate billion-fold amplification of the RNA target in less than two hours and does not utilize Taq polymerase or thermal cycling. It has been described as a self-sustained sequence reaction (3SR; Guatelli et al., *Proc. Natl. Acad. Sci. USA*, 1990, 87(5):1874–1878) and transcription-based amplification (TAS; Kwoh, D. Y. et al., *Proc. Natl. Acad. Sci. USA*, 1989, 86(4):1173–1177).

Key components of NASBA are the conversion of RNA into DNA by the action of reverse transcriptase and the production of RNA by T7 RNA polymerase. First, in the non-cyclic or linear phase of the reaction, a primer (P1) is bound at the 3' end of messenger RNA (mRNA). This primer is unusual in that it contains a T7 RNA polymerase promoter. Second, AMV reverse transcriptase converts the molecule to a RNA/DNA hybrid. RNAse H specifically degrades the RNA in the hybrid and the AMV reverse transcriptase converts the single stranded DNA into double stranded DNA. Finally, T7 RNA polymerase recognizes the T7 RNA polymerase promoter, initiating the cyclic phase. Antisense RNA product is produced and the AMV reverse transcript makes a DNA/RNA hybrid. RNAse H degrades the RNA, a duplex DNA molecule is synthesized, T7 RNA polymerase makes RNA, and the cycle continues.

The method combines current sample concentration and NASBA technology with novel nucleotide primers to amplify the viral RNA. Samples are obtained and can be concentrated by any method known in the art (for example, charged filters, filterite cartridges, vortex flow filtration, etc.) or, alternatively, left unconcentrated. The viral RNA is extracted by a combination of heating and Rneasy extraction. Utilizing novel enteroviral or noroviral primers, the RNA is amplified using NASBA technology. The RNA is then detected using a method known in the art (for example, by gel electrophoresis, molecular probing, or fluorescent molecular beacons).

In another aspect, the present invention provides primers, probes, molecular beacons, specific internal controls, and methods for detection and quantitation of noroviruses and enteroviruses in samples, such as biological or environmental samples. These methods (assays) are based upon the amplification of a portion of the viral RNA polymerase gene, using a method such as NASBA for amplification, and detection using a labeled (e.g., fluorescently labeled) molecular beacon. The norovirus assay of the invention can detect viruses within the genogroup II family of noroviruses, and can detect 0.1 fg. noroviral RNA (approximately $10^3$ virus particles). The enterovirus assay can routinely detect approximately 10 enteroviral particles. In one embodiment, the sample is an environmental sample, such as soil, food, beverages, feed, water (e.g., fresh water, salt water, waste water, drinking water), sewage, sludge, and surfaces or samples obtained from surface swipes. In another embodiment, the sample is a biological specimen, such as a clinical sample (e.g., stool, saliva, blood, urine, cerebrospinal fluid, etc.). In another embodiment, the sample comprises an organism or tissue from an organism, such as shellfish, which are potential hosts for noroviruses and enteroviruses.

BRIEF DESCRIPTION OF THE SEQUENCES

SEQ ID NO:1 is the nucleotide sequence for primer Ent P1 (=JP127).

SEQ ID NO:2 is the nucleotide sequence for primer Ent P2 (=JP128).

SEQ ID NO:3 is the nucleotide sequence for a probe specific for detecting poliovirus.

SEQ ID NO:4 is the nucleotide sequence for primer Ent P3.

SEQ ID NO:5 is the nucleotide sequence for EnteroBeacon.

SEQ ID NO:6 is the nucleotide sequence for primer Nor3.

SEQ ID NO:7 is the nucleotide sequence for primer Nor4.

SEQ ID NO:8 is the nucleotide sequence for NorBeacon.

SEQ ID NO:9 is the nucleotide sequence for the Enteroviral Internal Control.

SEQ ID NO:10 is the nucleotide sequence for the beacon for the enteroviral internal control.

DETAILED DISCLOSURE OF THE INVENTION

The subject invention provides polynucleotides and methods for detecting the presence of an RNA virus, such as enterovirus and norovirus, within a sample. The method of the invention can include a series of biochemical steps preparatory to commencing the detection assay. In one embodiment, the invention provides an isolated polynucleotide comprising a nucleic acid sequence selected from the group consisting of SEQ ID NOs: 1–10, or a fragment thereof. In another embodiment, the invention provides an isolated polynucleotide consisting of a nucleic acid sequence selected from the group consisting of SEQ ID NOs: 1–10, or a fragment thereof.

The method of the invention includes amplifying the viral RNA from the sample using an isolated polynucleotide (amplification primer and/or beacon) of the invention, which is capable of selectively hybridizing with the viral nucleic acids. Preferably, the polynucleotides are selected from the group consisting of SEQ ID NO:1, SEQ ID NO:4, and SEQ ID NO:5 (primer Ent P1, primer Ent P3, and EnteroBeacon, respectively), for detection of enterovirus. Preferably, the polynucleotides are selected from the group consisting of SEQ ID NO:6, SEQ ID NO:7, and SEQ ID NO:8 (primer Nor3, primer Nor4, and NorBeacon, respectively), for detection of norovirus.

Samples are obtained and are tested, either unconcentrated or after concentration by a method known in the art (for example, charged filters, filterite cartridges, vortex flow filtration, etc). Current sample concentration and NASBA technology is combined with novel nucleotide primers to amplify the viral RNA contained therein. The viral RNA can be extracted by a combination of heating and Rneasy extraction. Utilizing novel enteroviral and/or norovirus primers, the RNA is amplified using NASBA technology or other enzyme-based amplification reaction.

The method of the subject invention involves obtaining or providing a sample (also referred to herein as the test sample). The test sample can be taken from anywhere susceptible to contain viruses such as enterovirus and norovirus, for which there is a desire to detect the viral presence. For instance, such a test sample can be taken from a human or non-human subject, such as a companion animal (such as a dog or cat), drinking water, or livestock (e.g., bovine, porcine, etc.) facilities, livestock drinking water, the surrounding environment (pastures, water, etc.), from environmental specimens, from aquatic media in direct or indirect contact with the source of contamination, for example, effluents of the livestock facility containing livestock waste, rivers close to the source of contamination or crossing the possible source of contamination, food for humans, food for companion animals, food for livestock, etc. The source of contamination may be, for example, a livestock facility, typically a bovine or porcine livestock farm. The test sample can be surface matter that may contain or otherwise support the presence of the virus.

The test sample can be, any sample susceptible to containing an enteric virus, such as enteroviruses and noroviruses. For example, the test sample can be a biological sample, such as blood, saliva, urine, sputum, nasal mucus, feces (stool), host cells, host tissues, tissue homogenates, muscle, liver, thymus, cerebrospinal fluid, etc.; or an environmental sample such as an environmental specimen, a sample of pasture, a water sample, a sample of fish or molluscs found in potentially contaminated water, clothing, eating utensils, etc. The test samples can be subjected to purifying protocols known in the art or used in the detection analysis directly. For example, column chromatography, density centrifugation, or ammonium sulfate precipitation. These and other methods are disclosed, for example, in Sambrook et al., Molecular Cloning: A Laboratory Manual, Cold Spring Harbor Laboratory, New York (1989). For simplicity and ease of assay, it is preferred that the sample be used directly without purification.

The test sample is then subjected to an appropriate treatment to remove or extract the nucleic acid contained in the viral particles eventually present in the test sample. The RNA can be extracted by conventional methods, using conventional kits and reagents and then placed in contact with the reagents for amplification, e.g., NASBA, the reverse transcription (RT) reaction and for the polymerase chain reaction (PCR) in conditions in which a sequence of target nucleotides present in the genome of the enteric virus with an RNA genome is amplified to form an amplification product. The RT-PCR reaction can be performed using conventional methods, either in a single stage or in two stages. Those skilled in the art are familiar with both alternatives.

As used herein, the term "primer" means an isolated or purified polynucleotide which is produced synthetically or biologically and includes a specific nucleotide sequence which permits hybridization to a section containing the target nucleotide sequence. Defined primers/polynucleotides may be produced by any of several well known methods, including automated solid-phase chemical synthesis using cyanoethylphosphoramidite precursors. Other well-known methods for construction of synthetic primers/oligonucleotides may, of course, be employed (J. Sambrook, E. F. Fritsch and T. Maniatis, Molecular Cloning 11 (2d ed. 1989).

The primers and molecular beacons used to amplify the sample nucleic acids (e.g., SEQ ID NOs:1–10, or functional fragments thereof) may be coupled to a detectable moiety (a label). A preferred example of such a detectable moiety is fluorescein, which is a standard label used in nucleic acid sequencing systems using laser light as a detection system. Other detectable labels can also be employed to label the primers, molecular beacons, and probes of the invention, however, including other fluorophores, radio labels, chemical couplers such as biotin which can be detected with streptavidin-linked enzymes, and epitope tags such as digoxigenin detected using antibodies. The primers, probes, and molecular beacons may be modified whereby another nucleotide is added to or substituted for at least one nucleotide in the oligonucleotide. The term "add(ed)" means that nucleotide, oligo dGTP, oligo DATP, oligo dTTP, oligo dCTP, etc. having fluorescence substance, linker arm, biotin, etc. are bound to a 5'-terminal or a 3'-terminal of the oligonucleotide sequence. The term "substitute(d)" means that nucleotide having fluorescence substance, linker arm, biotin, etc. is introduced as a substitute for at least one nucleotide in the oligonucleotide. Introduction of known labels such as radioactive substances, enzymes, fluorescence substances, etc. after synthesis of the oligonucleotide is also included therein.

The reagent mix to perform the RT of the RNA of an enteric virus contains the reagents required for the reaction, for example water, dNTPs (dATP, dCTP, dGTP and dTTP), an appropriate buffer for the RT reaction, a reverse transcriptase, an initiator oligonucleotide (also known as a primer) which blends with a region of the RNA of the enteric virus in question and then, due to the reverse transcriptase, allows a DNA complementary (cDNA) to the RNA to be obtained, etc. On the other hand, the reagent mix for the PCR contains the reagents required for the reaction to take place, for example water, dNTPs, an appropriate buffer for the PCR reaction, a heat-stable polymerase DNA, a pair of primers to amplify the target sequence of the genome of the enteric virus in question, a magnesium salt, etc. In specific embodiments, the enteric virus is a enterovirus or norovirus.

In another embodiment, the method of the invention is performed using a single RT-PCR reagent mix containing the reagents required for the reaction to take place, for example water, dNTPs, an appropriate buffer for the RT-PCR reactions, a reverse transcriptase, a heat-stable polymerase DNA, etc. There are kits commercially available that provide this reaction mix, to which the appropriate primers are added. In this case, it is an advantage that the primers used for the RT reaction is one of the primers involved in the enzymatic amplification reaction (PCR).

To apply the method provided by this invention any primer that allows one to obtain a cDNA of the enteric virus in question can be used, and any pair of primers that allows amplification of a target sequence within the viral RNA polymerase gene of the enteric virus in question.

Conventional techniques can be used for the RT-PCR reaction, in conditions in which an amplifiable DNA fragment, eventually present in the reaction medium, representative of a target sequence of an enteric virus, is amplified to form an amplification product. The amplification product is separated and analyzed using conventional techniques, for example by electrophoresis, and sequenced. Next, the presence or absence in the test sample of an enteric virus containing the selected target sequence is determined and the viral isolate is identified. The identification of the isolate of the enteric virus(es) detected can be by conventional methods, for example by sequencing the region of the amplified viral genome. The detection of an enteric virus in the test sample indicates the existence of environmental contamination or infection.

Conventional techniques are used for the PCR, in conditions in which an amplifiable DNA fragment, eventually present in the reaction medium, representative of a target sequence of an enteric virus is amplified to form an amplification product. The amplification product is separated and analyzed using any conventional method, for example by electrophoresis, and sequenced, and the presence or absence of the enteric virus containing the selected target sequence is determined and the viral isolate identified. The identification of the isolate of the enteric virus(es) detected can be by conventional methods, for example by sequencing the region of the amplified viral genome. The detection of an enteric virus in the test sample can indicate the existence of environmental contamination or infection, for example, depending upon the nature and origin of the test sample. In a specific embodiment, the products of the RT-PCR reaction are separated by electrophoresis in agarose and viewed by conventional methods, for example ultraviolet light after staining with ethidium bromide.

The detection methods of the invention can be used in different applications, for instance to identify the existence of environmental contamination, or presence of infection, to discover the origin of the contamination, to conduct epidemiological studies or studies related to viral molecular evolution, etc.

As it is used in this description, the expression "certain degree of identity" means that the identity between the isolates of the enteric viruses detected and characterized in the test sample and the isolates of the enteric viruses found in said possible source of contamination is 50% or more, preferably 80% or more, and more preferably 95% or more, when the degree of identity is measured by molecular sequencing of the region of the viral genome used in this study. If another less conserved region of the genome of an enteric virus is used, these values could be somewhat different. Alternatively, other techniques may be used, for example molecular typification, serological, etc., allowing one to compare the isolates of enteric viruses and conclude that two isolates of different enteric viruses belong to the same genotype or serotype.

The invention further includes a kit for the detection of enterovirus and/or norovirus, comprising at least a pair of primers allowing one to amplify a target sequence of the cDNA of the virus in question.

The kits provided by this invention can be in pack-form containing a plurality of recipients (e.g., compartments), including recipients with one or more primers, probes, and/or labeled molecular beacons of the subject invention (e.g., SEQ ID NOs:1–10), recipients with all or part of the other reagents required for the method provided by this invention, for example water, dNTPs (dATP, dCTP, dGTP and dTTP), an appropriate buffer for the reaction (RT, PCR or RT-PCR), a reverse transcriptase, a heat-stable polymerase DNA, a magnesium salt, etc. Additionally and optionally, the kits provided by this invention can include recipients with nucleic acid (RNA, cDNA, DNA, etc.) from norovirus and/or enterovirus, well characterized for use as a positive control. In a specific embodiment, the control is a specific internal control of the subject invention, such as SEQ ID NO:9.

There are more than 70 known enteroviruses. In addition to the three different polioviruses, there are 61 non-polio enteroviruses that can cause disease in humans: 29 coxsackieviruses (23 coxsackie A viruses and 6 coxsackie B viruses, 28 echoviruses, and 4 other enteroviruses. The presence of each of these enteroviruses can be determined using the polynucleotides and methods of the subject invention.

In a preferred embodiment, the Norovirus to be detected is a genotype II strain selected from the group consisting of GII-1 (Hawaii virus), GII-2 (Melksham virus), GII-3 (Mexico virus), and GII-4 (Grimsby virus).

Optionally, the methods of the invention can be used to detect the presence of enterovirus and norovirus in a sample simultaneously or consecutively, in any order.

The terms "polynucleotide", "oligonucleotide", and "nucleic acid sequence" are used herein interchangeably to refer to nucleic acid sequences of any length. For example, DNA and/or RNA molecules are composed of various nucleotides and/or nucleotide analogs.

The term "fragments" as it relates to polynucleotides and nucleic acid molecules (including primers) is understood to mean those fragments which are specific for the particular enteric virus (e.g., enterovirus or norovirus) when used for methods to identify the presence of the enteric virus and specific for an enteric virus serotype when used in a method for serotyping an enteric virus. For example, fragments of a polynucleotide of the subject invention (i.e., a primer, probe, molecular beacon, internal control) can be up to one nucleotide less than the particular full length sequence. For example, fragments can comprise a contiguous/consecutive span of at least 8, 9, 10, 11, 12, 13, 14, 15, and up to one nucleotide less than the full length nucleotide sequence of SEQ ID NOs:1–10. In a specific embodiment, the fragments comprise a contiguous span of at least 18 nucleotides, and up to one nucleotide less than the full length nucleotide sequence of SEQ ID NOs: 1–10. Fragments should be of sufficient length to retain their function according to the methods of the invention. For example, fragments of primers retain the ability to amplify their target sequence. In specific embodiments, the fragments have one, two, three, four, or five nucleotides less than the full length nucleotide sequence of the given polynucleotide. Such fragments may be truncated at the 5' end, the 3' end, or both the 5' and 3' ends, for example. In a specific embodiment, the fragments comprise a contiguous span of at least 18 nucleotides of the 5' end of SEQ ID NOs:1–10. In another specific embodiment, the fragments comprise a contiguous span of at least 18 nucleotides of the 3' end of SEQ ID NO:1–10.

The term "molecular serotyping" as used herein is understood to mean serotyping by one of various molecular techniques rather than one of usual immunological techniques.

An "isolated" or "purified" nucleic acid or an "isolated" or "purified" polypeptide is a nucleic acid or polypeptide that, by the hand of man, exists apart from its native environment and is therefore not a product of nature. An isolated nucleic acid or polypeptide may exist in a partially purified or substantially purified form. An isolated nucleic acid or polypeptide may also exist in a non-native environment such as, for example, a transgenic host cell. The polynucleotides of the invention (e.g., SEQ ID NOs:1–10) are preferably in an isolated or purified form.

The term "label" refers to any atom or molecule that may be used to provide a detectable (preferably quantifiable) signal, and that may be attached to a nucleic acid or protein. Labels may provide signals detectable by fluorescence, radioactivity, colorimetry, gravimetry, X-ray diffraction or absorption, magnetism, enzymatic activity, and the like. For example, labels such as FAM (6-carboxyfluorescein), DABCYL (4-(4'-dimethylaminophenylazo)-benzoic acid), or other flurochromes may be utilized. For example, other flurochromes that can be added to the 5' end in place of FAM (e.g., in the beacon) include CRCG, Cy3, Cy5, Oregon Green, ROX, Texas Red, Cy 3.5, Cy 5.5, Hexachlorofluorescein, and TET. In place of DABCYL on the 3' end as a quencher, one can use Black Hole Quencher (BHQ), for example.

In one embodiment, the polynucleotides of the subject invention comprise a nucleic acid sequence selected from the group consisting of SEQ ID NO:1–10, or a functional fragment of SEQ ID NO:1–10, wherein the polynucleotide sequence includes a label at either the 5' end, the 3' end, or both the 5' and 3' ends.

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the reference sequence explicitly indicated.

The term "gene" is used to refer to any segment of nucleic acid associated with a biological function. The term "gene" encompasses the coding region of a protein, polypeptide, peptide or structural RNA. The term "gene" also includes sequences up to a distance of about 2 kb on either end of a coding region. These sequences are referred to as "flanking" sequences or regions (these flanking sequences are located 5' or 3' to the non-translated sequences present on the mRNA transcript). The 5' flanking region may contain control or regulatory sequences such as promoters and enhancers or other recognition or binding sequences for proteins that control or influence the transcription of the gene. The 3' flanking region may contain sequences that direct the termination of transcription, post-transcriptional cleavage and polyadenylation as well as recognition sequences for other proteins. A protein or polypeptide encoded in a gene may be full length or any portion thereof, so that all activities or functional properties are retained, or so that only selected activities (e.g., enzymatic activity, ligand binding, signal transduction, etc.) of the full-length protein or polypeptide are retained. The protein or polypeptide may include any sequences necessary for the production of a proprotein or precursor polypeptide. The term "gene" encompasses both cDNA and genomic forms of a coding region. A genomic form of a coding region may be interrupted with non-coding sequences termed "introns." The term "native gene" refers to gene that is naturally present in the genome of an untransformed cell. The primers of the subject invention amplify at least a portion of the RNA polymerase gene of the virus to be detected within the sample.

The terms "coding region" or "coding sequence" refers to the nucleotide sequence that codes for a protein of interest or to a functional RNA of interest, for example antisense RNA or a nontranslated RNA. The coding region of a protein is bounded on the 5' side by the nucleotide triplet "ATG" that encodes the initiator methionine and on the 3' side by one of the three triplets that specify stop codons (i.e., TAA, TAG, TGA). The coding region may be present in either a cDNA, genomic DNA or RNA form.

The terms "comprising", "consisting of" and "consisting essentially of" are defined according to their standard meaning. The terms may be substituted for one another throughout the instant application in order to attach the specific meaning associated with each term.

As used in this specification and the appended claims, the singular forms "a", "an", and "the" include plural reference unless the context clearly dictates otherwise. Thus, for example, a reference to "a primer" includes more than one such primer. A reference to "a polynucleotide" includes more than one such polynucleotide, and the like.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Following are examples that illustrate materials, methods, and procedures for practicing the invention. The examples are illustrative and should not be construed as limiting. Unless noted otherwise, all solvent mixture proportions are by volume and all percentages are by weight.

EXAMPLE 1

RNA Extraction and Amplification

In a preferred embodiment, NASBA technology, in combination with a concentration of the virus, is utilized. This step comprises filtering a desired volume of water (typically approximately 110 liters) by a method such as is known in the art (Filterite filter DFN 0.45-10UN; Filterite/MEMTEC A. Corp., Timonium, Md.; Standard Methods for the Examination of Water and Wastewater, 20$^{th}$ ed., American Public Health Assoc., Washington, D.C., 1998). Viruses are eluted with beef extract (pH 9.5) and concentrated using organic flocculation. As an alternative, the water can be filtered using vortex flow filtration (Paul, J. H. et al. *Appl. Environ. Microbiol*, 1991 57:2197–204. Concentration of viruses and dissolved DNA from aquatic environments by vortex flow filtration). The viral concentrate or standard poliovirus, for example, is stored at −20° C. until extraction.

Extraction is accomplished by taking a desired amount of the concentrate or enteroviral standard (for example, poliovirus), diluted to 100 µl in DEPC D1 (diethylpyrocarbonate-treated deionized water). An exemplary kit for accomplishing extraction comprises the Rneasy kit (Qiagen, Santa Clarita, Calif.). Dilutions of the enterovirus are made to concentrations of $9 \times 10^6$, $9 \times 10^4$, $9 \times 10^3$, and $9 \times 10^2$ enteroviruses in a 1.5-ml microfuge tube. Then 350 µl of RLT buffer, containing 10 µl β-mercaptoethanol per 1.0 ml RLT buffer, is added to the tubes, and the tubes are capped and placed in a 95° C. water bath for 10 minutes, followed by placement in an ice bath for 5 minutes. An amount of ethanol, here 250 µl, is added and mixed well by pipetting. This mixture (typically 700 µl), including any precipitate, is added to the spin column, and the tube is placed in a 2-ml collection tube, which is placed in a microfuge for 15 seconds at $\geq 10,000$ rpm. 700 µl of buffer RW1 is pipetted into the column and microfuged for 15 seconds at $\geq 10,000$ rpm to wash. Then 500 µl of RPE buffer is pipetted into the tube, using a new collection 2.0-ml tube, and microfuged for 15 seconds at $\geq 10,000$ rpm. 500 µl RPE is pipetted onto the column and centrifuged for 2 minutes at maximum speed to dry the column using the same collection tube. The mixture is transferred to a new 1.5-ml collection tube, with 30 µl Rnase-free water pipetted, and the tube is spun for 1 minute to elute. Then 1 U (unit) of Rnasin (PROMEGA) per microliter of sample is added.

Amplification of the enterovirus (here, for example, poliovirus) is preferably accomplished with the use of a kit (BIOMERIEUX (Durham, N.C.)), using two primer sequences, EntP1 (=JP127) and EntP2 (=JP128). ENTP1 comprises 5'-AAT-TCT-AAT-ACG-ACT-CAC-TAT-AGG-GAG-AAG-GAC-CGG-ATG-GCC-AAT-CCA-A-3'(SEQ ID NO:1); EntP2 comprises 5'-CCT-CCG-GCC-CCT-GAA-TGC-GGC-TAA-3'(SEQ ID NO: 2). The primers are gel purified. Lyophilized primers are taken up in sterile DEPC-D1 to a final concentration of 100 µM, and aliquotted. The aliquotted samples can be utilized immediately by diluting to 10 µM, or they can be frozen for future use. If frozen prior to use, they are thawed and diluted to 10 µM.

A clean workbench should preferably be set up with UV-sterilization and hot blocks set at 65° C. and 41° C. Using a kit such as the BIOMEREIEUX kit, add 50 µl accusphere diluent to lyophilized accusphere, and vortex well. Then 5 µl of each diluted (10 µM) EntP1 and EntP2 primers are added to 50 µl dissolved accusphere for a total of 60 µl, which is sufficient for 11–12 reactions.

80 mM KCl is prepared. For example, 80 mM KCl can be prepared utilizing the NASBA kit by adding 16 µl NASBA KCl and 14 µl NASBA water. The 90 µl primer/accusphere mix is combined with the 30 µl KCl. For a positive control, the control contained in the kit can be used. In this case, 50 µl NASBA water plus the lyophilized NASBA control are added.

The reaction is set up by adding 5 µl D1+10 µl of primer/KCl mixture to a sterile 1.5-ml microfuge tube, which serves as a blank. For a poliovirus or unknown sample, 5 µl D1+10 µl primer/KCl mixture is added to a sterile 1.5 ml microfuge tube. For a kit control, aliquot out 15 µl of the positive control mixture to a sterile 1.5 ml microfuge tube.

The tubes are placed in the 65° C. hot block for 5 minutes and in a 41° C. hot block for 5 minutes, and 5 µl of the NASBA enzyme mixture is added, with mixing accomplished preferably by flicking, not trituration. For most assays, this "hot start" is not necessary, however. The tubes are incubated in the 41° C. hot block for 5 minutes, then pulse spun in a microfuge for 1–2 sec, incubated for 90 minutes in the 41° C. hot block, removed from the hot block, and immediately utilized for detection. Alternatively, if the samples are not used immediately, they can be frozen at −80° C. immediately and stored.

It should be noted that utmost care should be taken to keep extraction areas separate from amplification areas. At all times, positive controls should be kept separated from other samples. For example, the positive controls should never be in the same rack as negatives or unknowns. To further decrease the chance of cross-contamination, aerosol pipette tips should be used, gloves worn, and gloves changed frequently.

Detection is accomplished using, for example, a 7% acrylamide gel, run for 3 to 5 hours, followed by ethidium bromide staining. Alternatively, dot blotting and probing can be used. A list of preferred probes is provided in Table 1 below. One probe useful for poliovirus comprises 5'-TAC-TTT-GGG-TGT-CCG-TGT-TTC-3' (SEQ ID NO: 3). The probes can be labeled, such as by using a TROPIX, Inc. (Bedford, Mass.), Southern Star Chemiluminesent Detection System, version A.2. Detection of specific enteroviral types can be accomplished by probing with specific viral-type oligonucleotide probes.

EXAMPLE 2

Methods to Detect and Quantitate Enteroviruses and Noroviruses by Real Time Nucleic Acid Sequence Based Amplification (NASBA)

This method has been developed to detect enteroviruses and genogroup II noroviruses from environmental samples. Environmental samples can be fresh or saline waters, surfaces, and stool samples. The methods should also be appropriate for clinical samples (blood, urine, cerebrospinal fluid, etc.)

A. Extraction of Viral RNA from Aqueous Samples

If samples are suspected to have high concentrations of viruses (e.g., raw sewage, wastewater, septage), then there is no need to concentrate. For concentration from seawater, a modified method of Katayama, H. et al. (*Appl. Environ. Microbiol.*, 2002, 68(3):1033–1039) is recommended.

B. Collection of Enteroviruses and Noroviruses from Seawater

1. Collect 500–1000 ml of the seawater to be tested (if larger volumes are to be sampled, increase the diameter of the filter and the filtration manifold to be used).
2. Using a sterile 47 mm filtration unit fitted with a sterile Millipore HA filter, filter the water sample using mild vacuum (10–15 psi).
3. When the filtration is complete, wash the filter by filtering through 200 ml of 0.5 mM $H_2SO_4$ to remove cations. This wash is discarded.
4. The filtration unit is connected to a small collection vacuum flask. 2.0 ml of 1 mM NaOH is added and filtered through the filter. The filtrate is neutralized with 50 mM $H_2SO_4$ and used in the RNA extraction protocol below.

C. Collection of Noroviruses from Stool Samples

1. Make sure all protocols are performed in a Biological Safety Cabinet.
2. Bring 100 to 500 ul of feces to 1.0 ml by adding sterile, RNase-free Phosphate Buffered saline (PBS).

3. It is convenient to divide this into two 500 ul aliquots in sterile 2 ml microcentrifuge tubes. Add 1.5 ml freon (1,12 trichlorotrifluoroethane) and mix well by vortexing.
4. Spin at 5000×G for 10 min in a microcentrifuge. Collect the upper aqueous phase, being sure not to transfer particulate matter. If the supernatant is clear, proceed to RNA extraction. If not, perform a second freon extraction.
5. Collect the supernatant and proceed to the RNA extraction protocol.

D. RNA Extraction Protocol

This protocol uses the Qiagen RNeasy Kit and protocol (RNeasy Mini Kit Qiagen Corporation #74106), whereas other RNA extraction protocols may be used.

1. 100 ul of the extract from stool samples or environmental samples as described above is added to 350 ul of the RLT buffer (containing β-mercaptoethanol) in the Qiagen RNeasy kit and briefly vortexed.
2. This mix is incubated at room temperature for 10 minutes.
3. 250 μl of 100% EtOH is added, and the entire 700 μl mixture placed onto an RNeasy column.
4. The column is centrifuged at 10,000 rpm for 30 seconds.
5. The flow through is discarded.
6. 700 μl of Buffer RW1 (from the RNeasy kit) is added to the column and the column centrifuged at 10,000 rpm for 30 seconds.
7. The collection tube is discarded and 500 μl Buffer RPE (+EtOH; RNeasy Kit) is added to the column.
8. The column is centrifuged at 10,000 rpm for 30 seconds and the flow through discarded.
9. Another 500 μl RPE is added to the column and the column centrifuged for 2 minutes at 10,000 rpm.
10. The collection tube is discarded and the column centrifuged again at full speed for 1–2 minutes.
11. The column is placed in a 1.5 ml collection tube and 50 μl of RNase free water is added directly to the column. The column is centrifuged at full speed for 1 minute.
12. RNA (2.5 μl) is then directly used for NASBA or diluted (1:10, 1:100) to dilute potential inhibitors.

E. NASBA Detection and Quantitation of Noroviruses

Instrumentation: Specialized instrumentation developed for Q-PCR (quantitative PCR) that enables incubation of samples at a controlled temperature while simultaneously measuring fluorescence is required. This includes but is not limited to the ABI Model 7700 Sequence Detection System, or the BioMerieux EasyQ reader (the latter only works for NASBA).

NASBA Regents: NASBA Reagents should include the BioMerieux Nuclisens Basic Kit (#285053)

NASBA Primers and Beacon: Primers and beacons can be synthesized by a manufacturer of oligonucleotides (e.g., Qiagen-Operon) and should, preferably, be gel-purified. Tables 2 and 3 list the sequences of the NASBA primers and Molecular Beacon for Enteroviruses and Noroviruses. It is recommend that the primers and beacon be dissolved in sterile RNase-free water at a stock concentration of 100 uM and aliquoted into small volumes and frozen at −80° C.

TABLE 1

Primers and Beacon for the amplification of the enterovirus 5' UTR (untranslated region)

| Primer | Sequence |
| --- | --- |
| Ent P1 | 5'AATTCTAATACGACTCACTATAGGGAGAAGGACCGGATGGCCAATCCAA-3' (SEQ ID NO:1) |
| Ent P3 | 5'-GGTGTCCGTGTTTCCTTTTA-3' (SEQ ID NO:4) |
| EnteroBeacon | 5'FAM-CATGCGTGGCTGCTTATGGTGACAATCGCATG-DABCYL-3' (SEQ ID NO:5) |

These primers will amplify a 106–108 base pair (bp) amplicon.

TABLE 2

Primers and Beacon for the amplification of the norovirus RNA polymerase gene.

| Primer | Sequence | |
| --- | --- | --- |
| Nor3 | 5' CAATGGAATTCCATCGCCCA 3' | (SEQ ID NO:6) |
| Nor4 | 5' AATTCTAATACGACTCACTATAGGG-AGAA-GTTGTCACGATCTCATCATCA 3' | (SEQ ID NO:7) |
| NorBeacon 2 | 5'-FAM-CATCGGACATCATACAGGCTAATTCCGATG-DABCYL-3' | (SEQ ID NO:8) |

FAM is 6-carboxyfluorescein, and DABCYL is 4-(4'-dimethylaminophenylazo)-benzoic acid. Other flurochromes that can be added to the 5' end in place of FAM in the beacon include, for example, CRCG, Cy3, Cy5, Oregon Green, ROX, Texas Red, Cy 3.5, Cy 5.5, Hexachlorofluorescein, and TET. In place of DABCYL on the 3' end as a quencher, one can use Black Hole Quencher (BHQ), for example.

These primers will amplify a 123 bp fragment of the Genogroup II RNA polymerase gene of many Noroviruses. The T7 Promoter region is underlined.

NASBA Protocol

1. Dilute primer stocks 1:4 (2 μl primer to 6 μl H$_2$O).
2. Dilute beacon stock 1:4 (1.5 μl beacon to 4.5 μl H$_2$O).

3. Dilute stock 12 mM ROX (5-[and 6]-carboxy-X-rhodamine) 1:100 (1 µl ROX to 99 µl H$_2$O).
4. Primer Mix: 4 µl each primer (25 µM), 1 µl Beacon (25 µM) and 1 µl ROX (120 µM) results in each primer becoming 10 µM, Beacon 2.5 µM and the ROX 12 µM.
5. Dilute the KCl (yellow capped tube in BioMerieux Nuclisens Basic Kit) 16 µl KCl to 14 µl H2O
6. Dilute the reagent sphere (Blue capped tube in BioMerieux Nuclisens Basic Kit) in 80 µl of diluent and vortex to mix well.
7. Add the entire 30 µl KCl mix to the reagent mix (Final Concentration 80 µM KCl).
8. Add the entire 10 µl primer mix (Concentrations at this point are 800 nM primers, 200 nM beacon, and 1 µM ROX).
9. Place 5 µl of this mix into 24 tubes 200 µl optical PCR tubes (such as Applied Biosystems Optical Tubes, part #4316567) (Final concentrations are 400 nM primers, 100 nM beacon and 500 nM ROX).
10. Add 55 µl of enzyme diluent to the enzyme sphere (Red capped tube in the BioMerieux Basic Kit) (start the timer for 20 min).
11. Add 2.5 µl of RNA extract (see above) or RNase-free DI water (blank) to each reaction tube.
12. After the 20 minutes (enzyme sphere dissolution time), start the precycle which is 2 minutes at 65° C. and then 41° C. for 2 minutes in the ABI 7700 or equivalent instrument.
13. During the precycle, aliquot 2.5 µl of enzyme into a strip of caps of optical tubes (such as Applied Biosystems Optical Caps, part no. 4323032).
14. Add enzyme to the tubes by spinning from the caps.
15. Start NASBA for 41° C. for 90 min in the ABI 7700 or equivalent instrument.
16. Running a series of standards or dilutions of a known positive stool sample is recommended. Alternatively, one can make transcript in vitro from cloning a portion of the RNA polymerase gene.
17. When the cycle is complete, analyze the data, set an appropriate threshold fluorescence, and relate the standards to the time to positivity (time at which samples display a significant increase in fluorescence). Plot the time to positivity vs. the log concentration of the standard. Use this regression to calculate the approximate viral load (or RNA concentration) in unknown samples.

Results Obtained with the Method

Standard curves were prepared with Poliovirus S1 that were counted by epifluorescence microscopy. A typical standard curve appears in FIG. 2B.

TABLE 3

Specificity of amplification using enteroviruses

| Enterovirus | Source | # of particles | Amplification |
|---|---|---|---|
| Coxsackie B4 | T. Scott | $2.2 \times 10^4$ | + |
| Coxsackie B5 | T. Scott | $1.55 \times 10^5$ | + |
| Echovirus 1 | T. Scott | $2.32 \times 10^5$ | + |
| Echovirus 4 | T. Scott | $9.19 \times 10^4$ | + |
| Echovirus 5 | T. Scott | $1.07 \times 10^5$ | + |
| Echovirus 7 | T. Scott | $2.53 \times 10^5$ | + |
| Echovirus14 | T. Scott | $1.91 \times 10^5$ | + |
| Echovirus 26 | T. Scott | $6.69 \times 10^4$ | + |
| Poliovirus1 | T. Scott | $5.6 \times 10^4$ | + |
| CoxsackieB1 | ATCC VR-28 | $6.5 \times 10^4$ | + |
| CoxsackieB2 | ATCC VR-29 | $3.0 \times 10^4$ | + |
| CoxsackieB3 | ATCC VR-30 | $5.4 \times 10^4$ | + |
| CoxsackieA9 | ATCC VR-186 | $3.7 \times 10^4$ | + |
| CoxsackieA16 | ATCC VR-174 | $5.5 \times 10^4$ | + |
| Enterovirus 70 | ATCC VR-836 | $1.6 \times 10^5$ | + |
| Enterovirus 71 | ATCC VR-784 | $3.6 \times 10^4$ | + |

Table 3 shows the specificity of the primers toward enteroviral targets. Sixteen of 16 enteroviruses were detected by the method. Table 4 shows the specificity or lack of reactivity toward non-enteroviral targets. No non-enteroviral targets tested amplified using the EntP1/EntP3 primer sets.

TABLE 4

Negative viruses tested by the Enterovirus Real Time NASBA assay.

| Name | Strain | Source | Amplification |
|---|---|---|---|
| (−) Control | | USF-DOH | — |
| Norovirus G2 | G2 | USF-DOH | — |
| Herpesvirus | | USF-DOH | — |
| Influenza A (H1N1) | A | USF-DOH | — |
| Influenza B | B | USF-DOH | — |
| Rotavirus | | USF-DOH | — |
| Adenovirus | | USF-DOH | — |
| Rhinovirus | | USF-DOH | — |
| Hepatitis A | | USF-DOH | — |
| Reovirus | | USF-DOH | — |
| Dengue | | USF-DOH | — |

Current detection methods for norovirus do not permit quantification of virus. To overcome this limitation, the present inventors have taken an approach in which a standard curve is produced based on known transcript concentrations from which unknown samples can then be extrapolated to determine virus concentrations. This method assumes that each viral particle renders one copy of the target sequence. To generate a transcript standard, primers were designed to specifically amplify the target region amplified in the NASBA reaction plus approximately 100 bases of the flanking RNA both up and downstream. Reverse transcription PCR with these primers resulted in a 350 base pair product that was subsequently cloned into pCRII (INVITROGEN Corporation, Carlsbad, Calif.). Using an internal SP6 promoter region on the vector, in vitro transcript of the Norovirus target region was generated and quantified.

Figure 1:
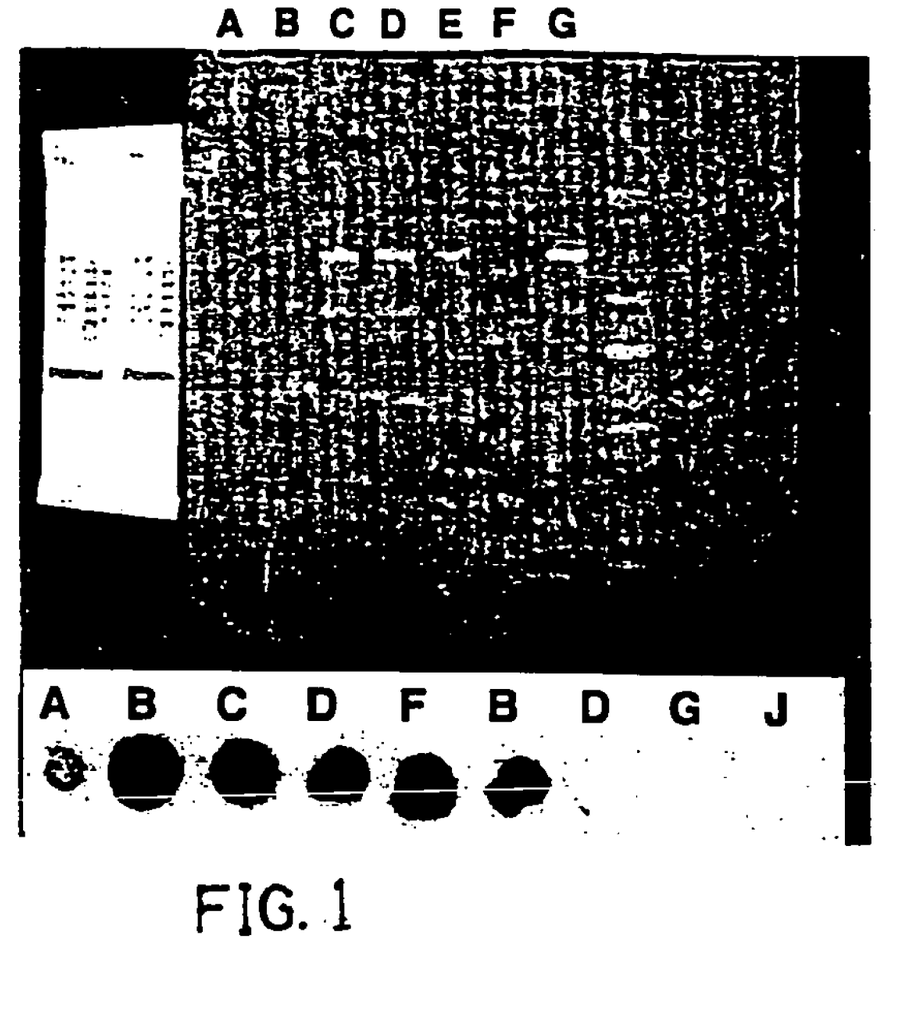
FIG. 1 is a gel electrophoresis illustrating the effects of NASBA amplification of enteroviral genomes.
Figure 2A:
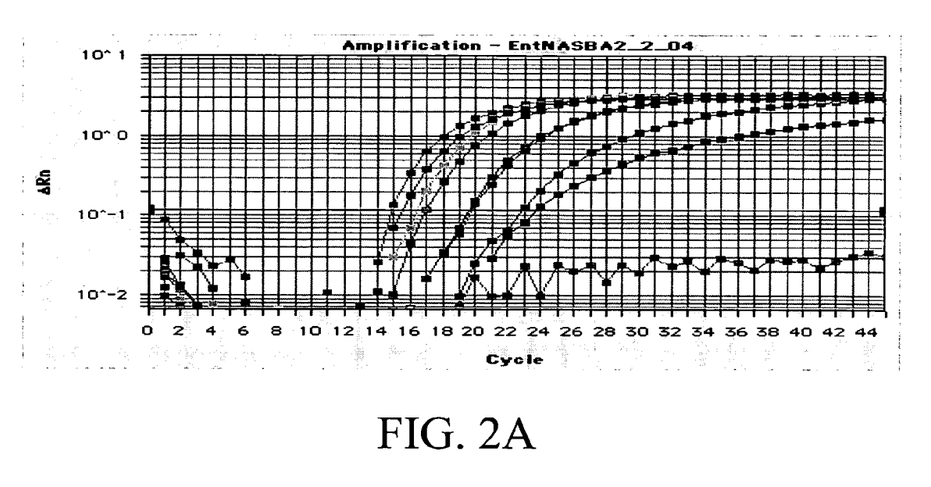
FIGS. 2A and 2B show, respectively, an amplification plot and standard curve of enteroviruses based upon viral direct counts.
Figure 2B:
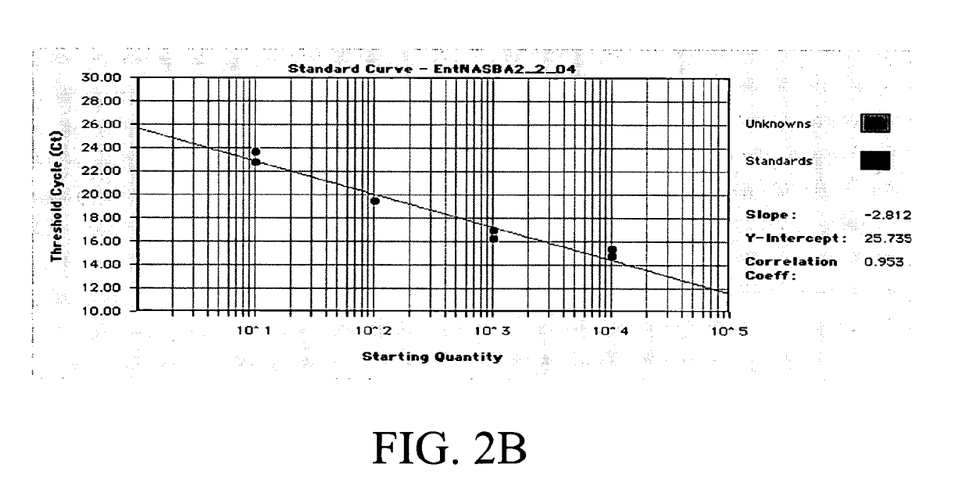
Figure 3:
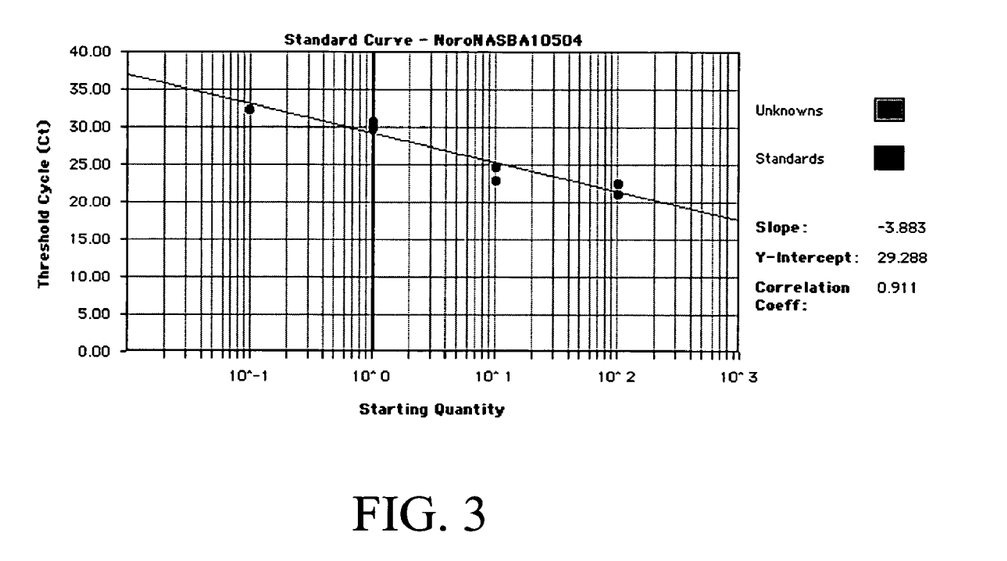
FIG. 3 shows the standard curve of a norovirus transcript. Each concentration is in duplicate from 100 fg to 0.1 fg.

Standard curves using serially diluted transcript from 1 pg to 0.01 fg were generated. $R^2$ values were typically around 0.9 (FIGS. 2A and 2B). The NASBA assay could routinely detect 1 fg transcript (approx. $10^4$ viral particles). Furthermore, 0.1 fg was detected in most runs (75%). The present inventors have compared these detection limits to those obtained using a side-by-side real time PCR (Taqman) assay for norovirus detection and have determined that the sensitivity of each assay is similar.

Noroviruses are a genetically diverse group of viruses. This sequence divergence has somewhat hampered the progress of the development of reliable nucleic acid sequence based detection methods. To evaluate this method's ability to overcome this issue, the present inventors extracted virus from 114 contaminated fecal samples. Raw stool samples collected from outbreak patients in Florida over the past four years were Freon-extracted to remove most contaminants. RNA was then extracted from the viruses using the RNeasy extraction protocol (QIAGEN Corporation, Valencia, Calif.). To date, forty-five of these samples have been evaluated using the method of the invention. In these tests, 78% of the samples tested positive for norovirus by NASBA. Sequence analysis on five of the negative samples revealed that the beacon region was significantly different from the probe sequence. The other negative samples are currently being evaluated in the same manner.

EXAMPLE 3

Quantitative Detection of Enteroviruses by Real Time NASBA Using an Internal Control (IC-NASBA)

Because of the three enzymes involved in NASBA, each with their different kinetics, the time to positivity (TTP) approach taken in Quantitative (Real-Time) PCR does not provide ideal standard curves with NASBA. Data sets typically have reaction kinetics that do not easily lend themselves to a simple threshold cycle (Ct) analysis. This results in standard curves with lower coefficients of determination ($r^2$=0.7–0.8) for NASBA compared to those for Real-Time PCR (typically >0.95).

Figure 4:
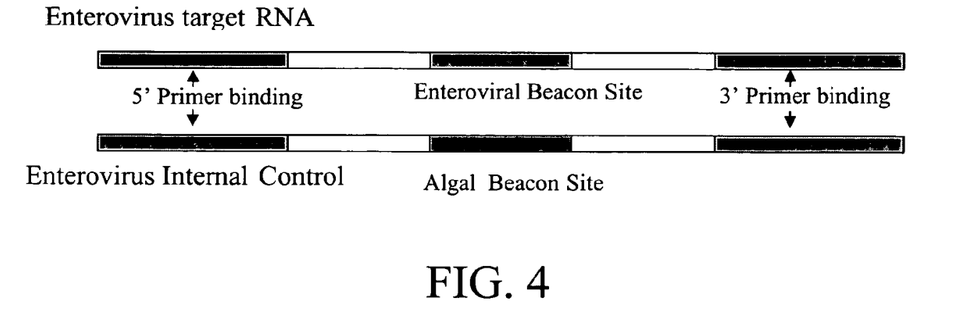
FIG. 4 shows a schematic of an internal control for enterovirus IC-NASBA, according to the subject invention.

The present inventors have designed a specific internal control containing a different beacon hybridization site. Thus, the same amplification primers are used for both the calibrator and the target mRNA. However, a second molecular beacon containing a different fluor (6-ROX) is used, which hybridizes to the unique internal site in the calibrator molecule (FIG. 4). The amplification of both the calibrator and the target are measured simultaneously by measuring fluorescence at two differing wavelengths (thus the need for two fluorescence channels in the sensor). The present inventors have made a synthetic RNA internal control for enteroviruses that contains the beacon site for an algal RNA (as shown below).

ality by PCR screening using an internal upstream M13 reverse primer and the assay's downstream (T7) primer. Two clones appearing to have the insert in the correct orientation were grown overnight in LB supplemented with 50 µg/ml of Kanomycin and the plasmid was extracted using the Wizard Midi-plasmid purification kit (PROMEGA Corporation, Madison, Wis.). The plasmid was sequenced using the internal vector M13 reverse primer to insure the insert's integrity. The plasmid was then linearized by digestion with NotI, the enzyme removed using the Wizard DNA clean-up kit (PROMEGA Corporation, Madison, Wis.), and run-off transcripts generated from an upstream SP6 promoter using the Riboprobe in vitro transcription kit (PROMEGA Corporation, Madison, Wis.). RNA was quantified and stored as described earlier.

B. Primer Mix and Beacons

1. Primers (e.g., ENTP1 and ENTP3; SEQ ID NOs:1 and 4, respectively) are diluted for final concentrations of 400 nM.
2. Both beacons (e.g., SEQ ID NOs:5 and 10) are diluted for final concentrations of 100 nM.
3. Internal control dilution is dependent on specific assay—for enteroviruses, addition of $10^4$ copies/reaction is suitable.
4. 4 µl of each primer and 1 µl of each beacon are added to the primer mix (no 6-Rox is added).
5. 1 µl diluted internal control is added to the primer mix for a total volume of 11 µl.

C. Reagent Mix

16 µl KCl stock solution is mixed with 13 µl NASBA water. The whole volumes of primer mix (11 µl) and KCl solution (29 µl) are added to the 80 µl reagent mix for a final volume of 120 µl, the same as if the bioMerieux protocol is followed.

1. Add the entire 10 µl primer mix (concentrations at this point are 400 nM primers, 100 nM beacon).

---

A. Methods for IC-NASBA

---

Enteroviral Internal control:

5'GGTGTCCGTGTTTCCTTTTATTTTTATTGCTTAGTCTCGGGTT   (SEQ ID NO:9)
ATTTTTTCACAGATTGTTATCATAAAGCGAATTGGATTGGCCATC
CGGT-3'

Enteroviral Internal control Beacon:

5'-ROX-CGATCGCTTAGTCTCGGGTTATTTTTTCGATCG-       (SEQ ID NO:10)
DABCYL-3'

---

To generate the internal control molecule, two oligonucleotides were designed that spanned the entire calibrator sequence and contained a 20 base overlap with each other. The oligos (serving as both template and primers) were placed in a PCR reaction (100 pmols each) and run under standard PCR conditions with an annealing step of 55° C. for twenty cycles. Reaction products were visualized on a 1% agarose gel stained with Ethidium Bromide. Amplicons were TA TOPO cloned into the pCRII cloning vector according to the manufacturer's instructions (Invitrogen Corporation, Carlsbad, Calif.). Clones were checked for direction- 2. Place 5 µl of this mix into 24 tubes 200 ul optical PCR tubes (such as Applied Biosystems Optical Tubes, part #4316567).
3. Add 55 µl of enzyme diluent to the enzyme sphere (Red capped tube in the BioMerieux Basic Kit) (start the timer for 20 minutes).
4. Add 2.5 µl of RNA extract (see above) or RNase-free DI water (blank) to each reaction tube.
5. After the 20 min (enzyme sphere dissolution time) start the precycle which is 2 minutes at 65° C. and then 41° C. for 2 min in the ABI 7700 or equivalent instrument.

6. During the precycle, aliquot 2.5 µl of enzyme into a strip of caps of optical tubes (such as Applied Biosystems Optical Caps, part no. 4323032).
7. Add enzyme to the tubes by spinning from the caps.
8. Start NASBA for 41° C. for 90 min in the ABI 7700 or equivalent instrument.
9. It is recommended to run a standard curve using extractions of log dilutions of the enterovirus, usually from $10^4$ to $10^2$ viruses calculated to be in the 2.5 µl RNA extract.

D. Results

Figure 5:
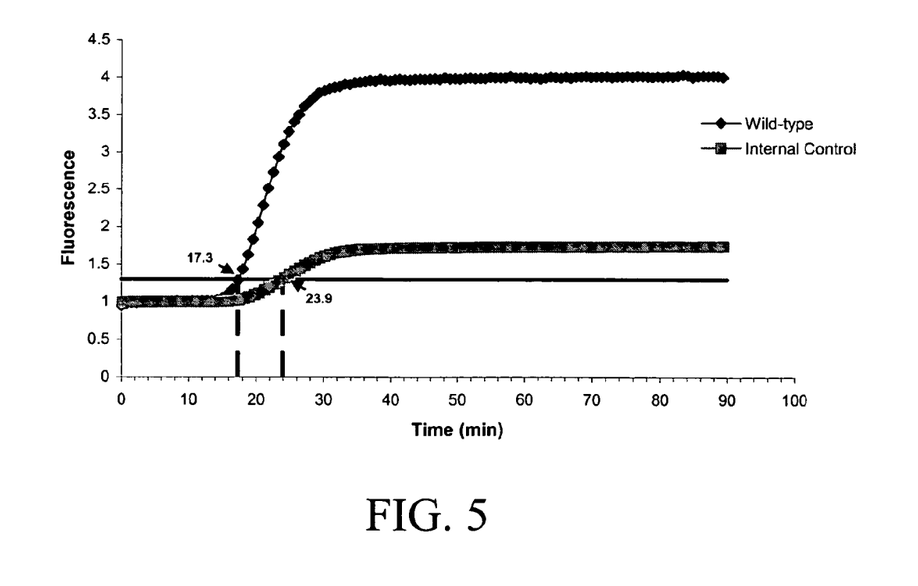
FIG. 5 shows the results of a typical IC-real time NASBA reaction containing 10,000 internal control copies. Dashed lines indicate the threshold cycle (Ct) for each of the wild-type and internal control.
Figure 6A:
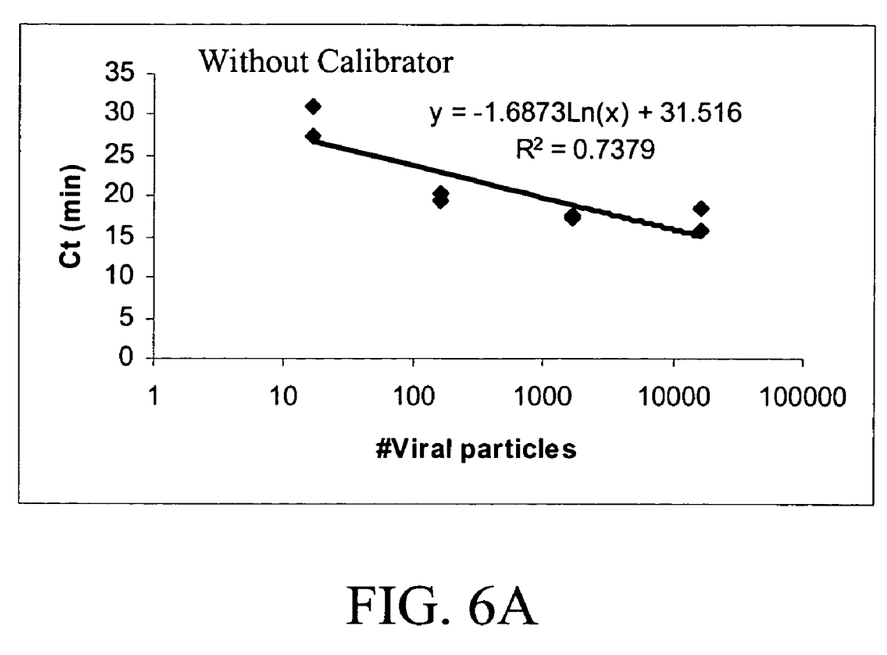
FIGS. 6A and 6B show standard curves of enteroviral RNA signals plotted against the Ct (FIG. 6A) and against the Ct ratio (FIG. 6B). A much better relationship is apparent in the Ct ratio method ($R2=0.9882$ for Ct ratio [IC-NASBA] vs. 0.7379 for Ct value method.
Figure 6B:
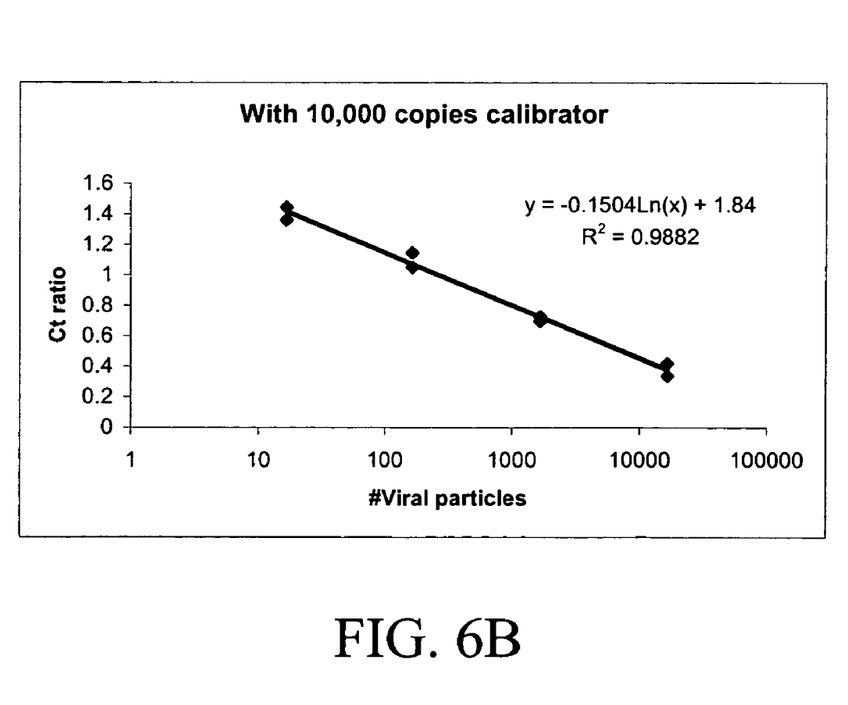

FIG. 5 shows the results of a typical IC-NASBA reaction containing 10,000 Internal Control copies. The ratio of the Ct of known standards to the Ct of the internal control is plotted against the standard concentration. This ratio is linearly correlated with concentration. Thus, once this relationship is established, it is used to determine the concentration of unknowns. FIGS. 6A and 6B show standard curves of enteroviral RNA signals plotted against the Ct (FIG. 6A) and against the Ct ratio (FIG. 6B). A much better relationship is apparent in the Ct ratio method ($R^2$=0.9882 for Ct ratio [IC-NASBA] vs. 0.7379 for Ct value method.

All patents, patent applications, provisional applications, and publications referred to or cited herein are incorporated by reference in their entirety, including all figures, tables, and sequences to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. An isolated polynucleotide comprising the nucleic acid sequence of SEQ ID NO: 5.

2. A method for detecting the presence of an Enterovirus in a sample, comprising contacting a polynucleotide region of the 5'-untranslated region of the Enterovirus genome with amplification primers; amplifying the polynucleotide region of the 5'-untranslated region and detecting the presence of an amplified polynucleotide using a labeled molecular beacon comprising the nucleic acid sequence of SEQ ID NO: 5, where the presence of the amplified product is indicative of the presence of the Enterovirus in the sample.

3. The method of claim 2, wherein the amplification primers are selected from the group consisting of SEQ ID NO:1, SEQ ID NO:2, and SEQ ID NO:4, or a fragment of any of the foregoing.

4. The method of claim 2, wherein said amplifying comprises nucleic acid sequence based amplification (NASBA).

5. The method of claim 2, wherein said amplifying comprises RT-PCR.

6. The method of claim 2, wherein said detecting comprises hybridization of the amplified product with a probe.

7. The method of claim 6, wherein said detecting comprising serotyping the Enterovirus with a probe specific for an Enterovirus serotype.

8. The method of claim 2, wherein the sample is a biological sample.

9. The method of claim 2, wherein the sample is an environmental sample.

10. The method of claim 2, wherein the Enterovirus is selected from the group consisting of Polio 1, 2, 3; Coxsackie A 1, 2, 3, 4, 5, 6, 7, 8, 9, 10, 11, 12, 13, 14, 15, 16, 17, 18, 19, 20, 21, 22, 23, 24; Coxsackie B 1, 2, 3, 4, 5, 6; ECHO 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34; Entero 68, 69, 70, 71; and Entero 72 (Hepatitis A).

11. The method of claim 2, wherein said method further comprises determining the quantity of Enterovirus within the sample.

12. The polynucleotide of claim 1 wherein the polynucleotide is labeled.

13. The polynucleotide of claim 1 wherein the polynucleotide is labeled with 6-carboxyfluorescein and 4-(4'-dimethylaminophenylazo)-benzoic acid.

14. The method of claim 2 wherein the molecular beacon is labeled with 6-carboxyfluorescein and 4-(4'-dimethylaminophenylazo)-benzoic acid.

* * * * *

UNITED STATES PATENT AND TRADEMARK OFFICE
CERTIFICATE OF CORRECTION

| | |
|---|---|
| PATENT NO. | : 7,205,112 B2 |
| APPLICATION NO. | : 10/938005 |
| DATED | : April 17, 2007 |
| INVENTOR(S) | : John H. Paul, III, Erica T. Casper and Stacey S. Patterson |

It is certified that error appears in the above-identified patent and that said Letters Patent is hereby corrected as shown below:

<u>Column 1</u>
Lines 21 - 22, "government may have certain" should read -- government has certain --.

<u>Column 23</u>
Lines 8 - 9, "detecting comprising" should read -- detecting comprises --.

Signed and Sealed this

Thirty-first Day of March, 2009

JOHN DOLL
*Acting Director of the United States Patent and Trademark Office*